United States Patent [19]
Andrese

[11] Patent Number: 6,015,423
[45] Date of Patent: Jan. 18, 2000

[54] DILATATION CATHETER TIP FOR ANGIOPLASTY PROCEDURES

[76] Inventor: Craig A. Andrese, 128 Stirrup La., Burr Ridge, Ill. 60521

[21] Appl. No.: 09/076,421

[22] Filed: May 12, 1998

Related U.S. Application Data
[60] Provisional application No. 60/081,442, Apr. 10, 1998.
[51] Int. Cl.[7] .................................................. A61M 29/00
[52] U.S. Cl. .......................................... 606/198; 606/194
[58] Field of Search ................................... 606/191, 192, 606/198, 159

[56] References Cited

U.S. PATENT DOCUMENTS

| | | | |
|---|---|---|---|
| 2,689,568 | 9/1954 | Wakefield | 606/198 |
| 5,176,128 | 1/1993 | Andrese . | |
| 5,279,565 | 1/1994 | Klein et al. | 606/198 |
| 5,447,503 | 9/1995 | Miller . | |
| 5,584,803 | 12/1996 | Stevens et al. | 606/192 |

FOREIGN PATENT DOCUMENTS

2945237A1 11/1979 Germany ...................... A61B 17/22

*Primary Examiner*—Michael Buiz
*Assistant Examiner*—Vy Q. Bui
*Attorney, Agent, or Firm*—Patnaude & Videbeck

[57] ABSTRACT

A dilitation catheter is disclosed including an elongate tubular body and a control rod extending therethrough from a proximal control end to a distal operating end. Adjacent the distal operating end is a pair of rigid or semi-rigid jaws which when closed substantially extend to a point. The jaws are hinged together at there rear by one of a pair of pivotal hinges or a resilient tubular section which allows the jaws to move between a closed position and an open position axial movement of the control rod. In one aspect of the invention, a resilient connection between the jaws and the elongate tubular body is foraminous to allow flow of bodily fluids through the operating jaws end of the catheter while the jaws are expanding luminal walls in a patient's body. Also, a guide wire may be utilized through the elongate tubular body and the operating jaws to provide for more exact placement of the operating end of the catheter.

14 Claims, 4 Drawing Sheets

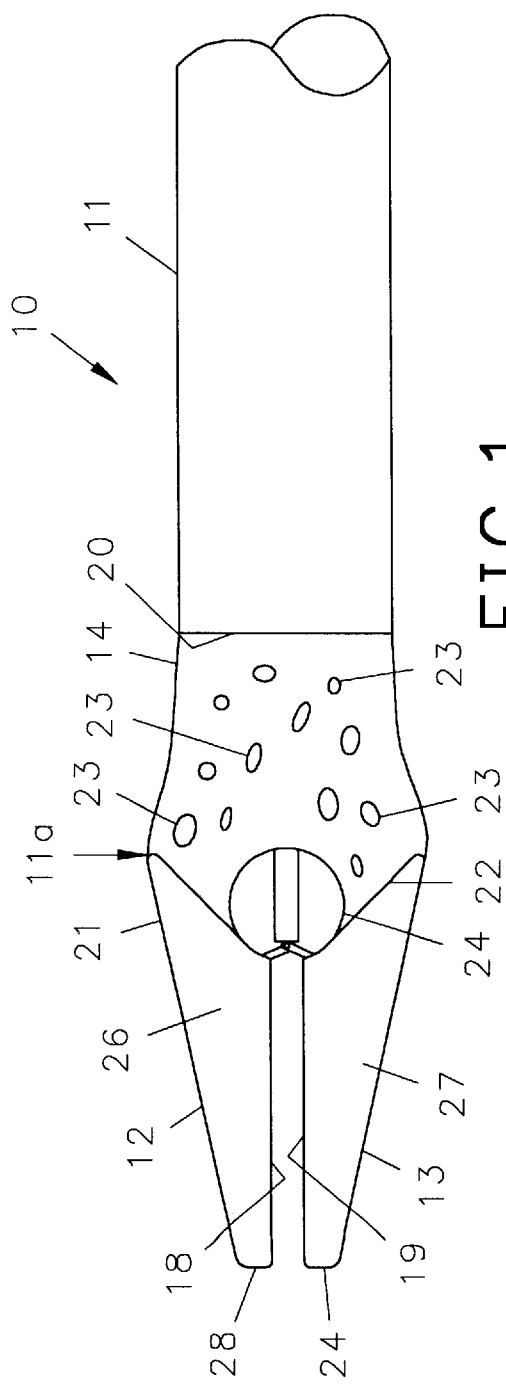
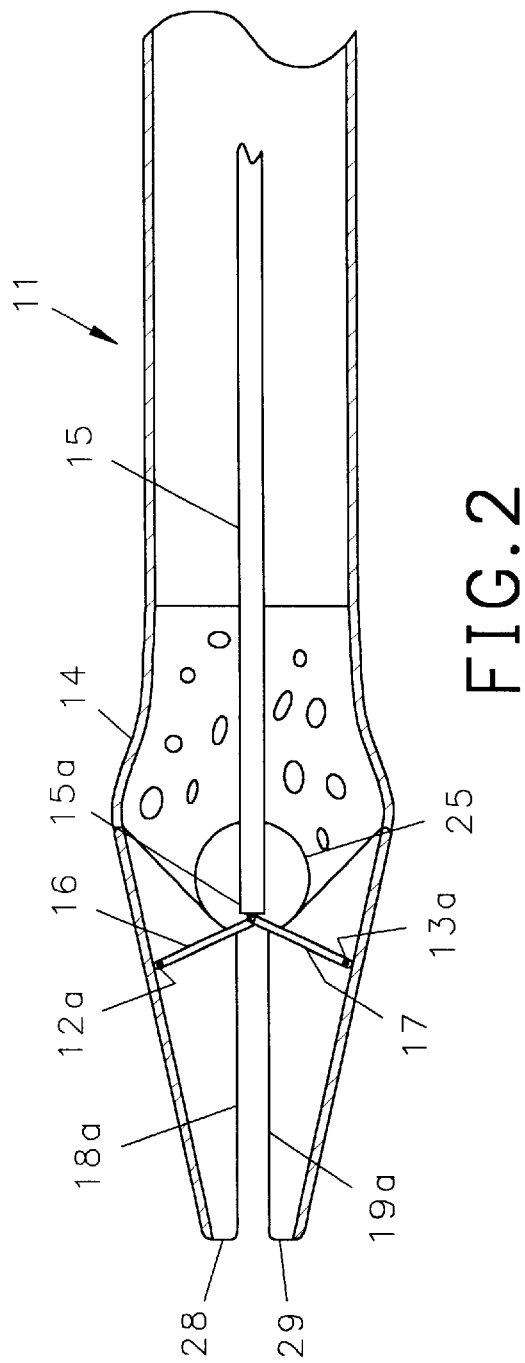
FIG. 1
FIG. 2

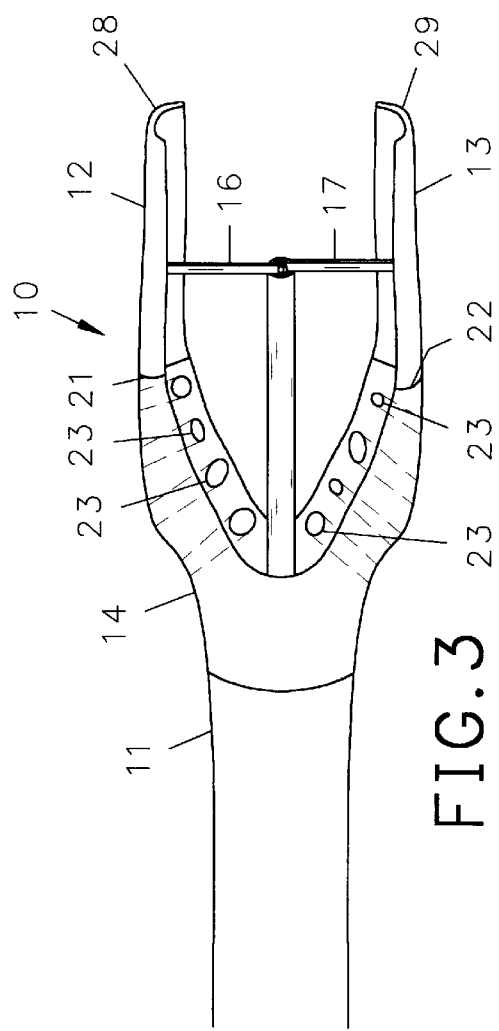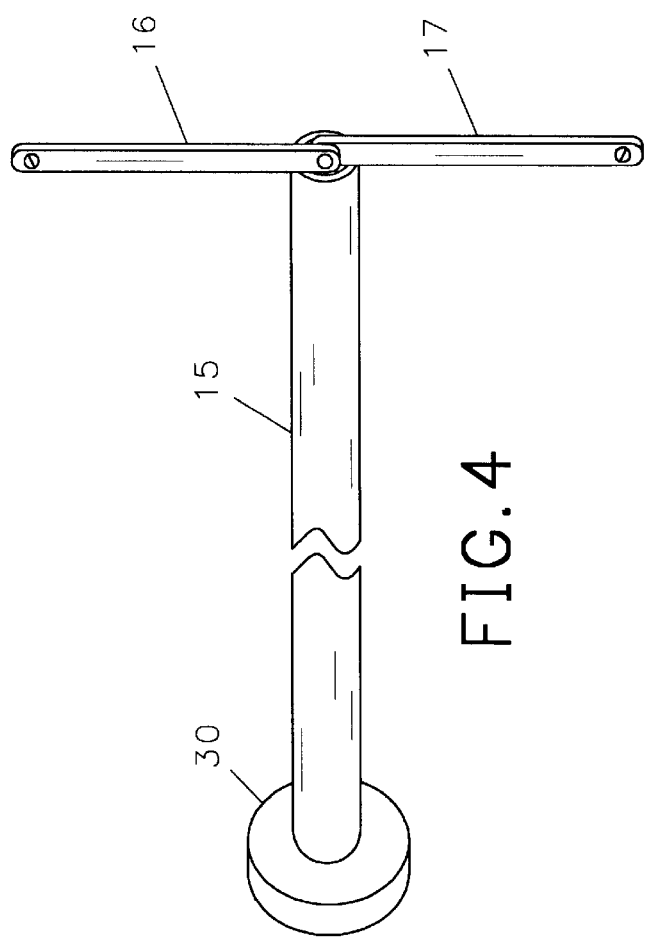

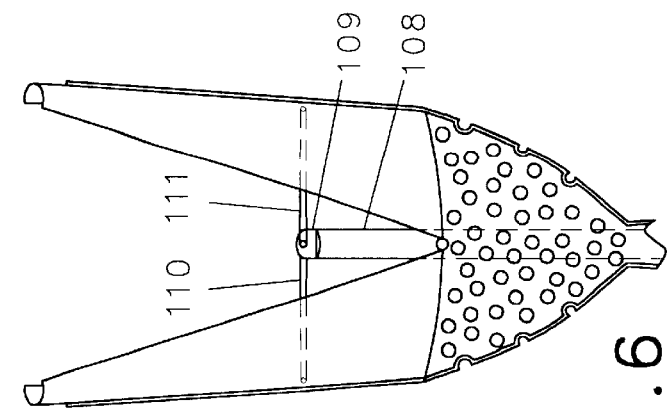
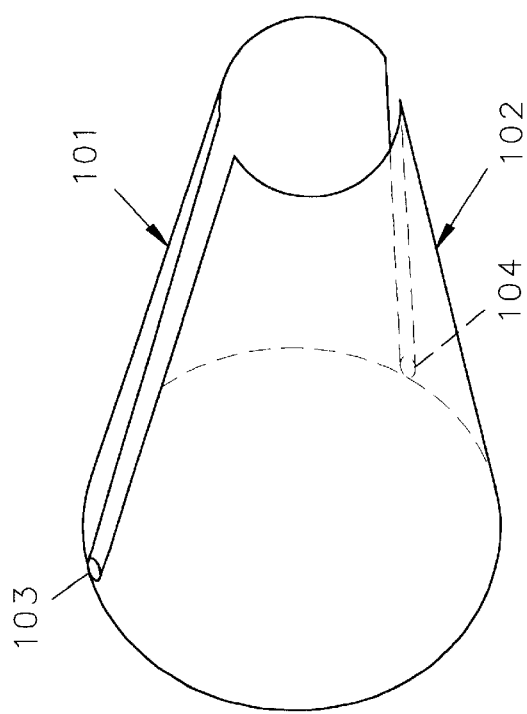
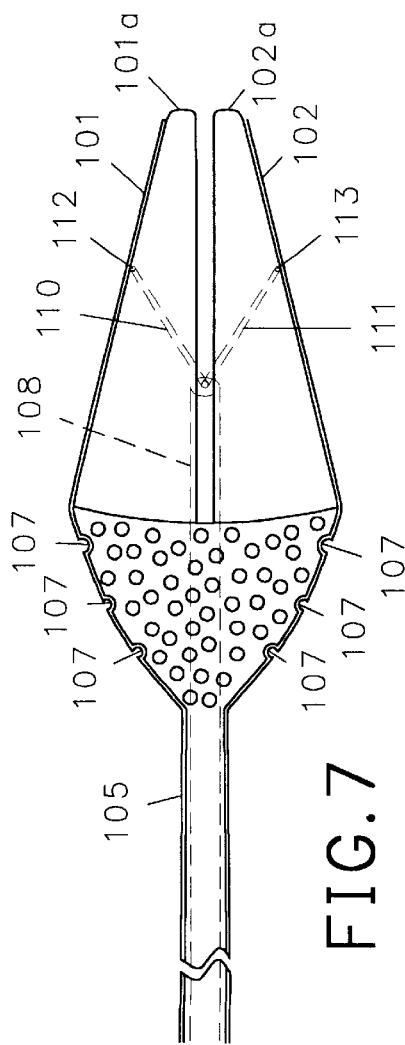

DILATATION CATHETER TIP FOR ANGIOPLASTY PROCEDURES

This application claims the benefit of U.S. Provisional Application No. 60/081442 FILING DATE Apr. 10, 1998.

The present invention relates to surgical instruments for angioplasty and, more particularly, to an improvement in a catheter having a tapered distal tip with an expandable lumen for use in angioplasty and other luminal dilitation procedures.

BACKGROUND OF THE INVENTION

Heretofore, catheters used in angioplasty and other dilatation type surgical procedures have generally had a conical tip. During an angioplasty procedure, a catheter is passed through the interior of a vessel to a partially obstructed or stenotic portion of the vessel. If an opening through that narrowed portion is nonexistent or too small for the cone shaped tip of the catheter to be pushed therethrough, the angioplasty procedure cannot be successfully employed. In typical angioplasty procedures, if the stenotic portion of the blood vessel can be breached by the tip of the catheter, an expandable balloon stored interiorly and rearwardly of the tapered tip may be positioned inside the stenotic portion of the vessel. The tapered tip, if made of an expandable lumen, such as found in U.S. Pat. No. 5,447,503, may be withdrawn from around the balloon. Thereafter, the balloon may be expanded by being filled with a fluid under pressure. This pressure then expands the balloon which applies pressure universally along the entire surface of the balloon and hopefully to the internal luminal wall.

This pressure, applied once or in doses, forces open the stenotic lumen in the hope that the patency of the lumen will remain open. One drawback of this instrument is that the balloon completely occludes the blood vessel in its expanded position, so its use in a surgical procedure is limited.

In my prior patent U.S. Pat. No. 5,176,128, I disclosed an organ retractor which is capable of being positioned through a trochar into a body cavity wherein it is expandable to allow the retractor to move aside and reposition organs during surgical procedures. In my copending patent application, Ser. No. 60/081,442 filed Apr. 10, 1998, I disclose an improvement in an organ retractor having a pair of hollow semi-frustoconical arms positioned around an internal stem with a mechanical means for extending the arms after that portion of the retractor has been positioned through the hollow cylindrical trochar.

Catheters for use in angioplasty are overwhelmingly of the balloon type, such as shown in the aforementioned U.S. Pat. No. 5,447,503. While these catheters may be used in blood vessels which are not completely closed, they have a limitation where stenotic portions of the vessel walls are too narrow to allow the tip to be pushed therethrough. Also, the balloon cannot function as a tip to allow it to be placed where most needed in the first instance.

A need has developed for an improved catheter tip suitable for use in angioplasty and other dilatation type surgical procedures. It is, therefore, an object of the present invention, generally stated, to provide an improved catheter with a mechanical distal end or tip.

Another object of the present invention is the provision of an improved catheter for use in connection with angioplasty and other dilatation type surgical procedures wherein the catheter is expandable while still allowing blood or other body fluids to flow through the stenotic area during the procedures.

SUMMARY OF THE INVENTION

The present invention is directed to an improved catheter tip for use in angioplasty and other dilatation type surgical procedures wherein the tip is formed of a pair of opposed hollow semi-frustoconical lumens which are mechanically expandable utilizing an internal wire or rod passed through the interior of the hollow catheter. A pair of opposed links extend from a pivotal mounting on the distal end of the rod to a pivotal mounting on the interior surface of each of the opposed tapered tips. Pushing the inner wire inwardly relative to the outer hollow catheter tube provides a radially outwardly directed vector through the linkage to expand the hollow semi-frustoconical tip ends. Mediate each of the rigid tip ends and the tubular catheter is positioned a resilient bridging portion which is hollow, cylindrical in shape, and foraminous to allow the passage of blood through the catheter tip during the angioplasty procedures.

BRIEF DESCRIPTION OF THE DRAWINGS

The features of the present invention which are believed to be novel are set forth with particularity in the appended claims. The invention, together with further objects and advantages thereof, may best be understood by reference to the following description taken in connection with the accompanying drawings, wherein like reference numerals identify like elements throughout, and in which:

FIG. 1 is an elevational front view of a first embodiment of the tip of a catheter constructed in accordance with the present invention;

FIG. 2 is an elevational view, shown in in cross section, of the catheter tip shown in FIG. 1;

FIG. 3 is an enlarged perspective view of the catheter tip shown in open position; and FIG. 4 is an enlarged elevational view of the tip operator rod and linkage.

FIG. 5 is an enlarged detailed diagramatic perspective view of a second embodiment of the catheter tip shown in substantially closed position.

FIG. 6 is an enlarged fragmentary elevational view of a second embodiment of the catheter tip of FIG. 5 shown in open position.

FIG. 7 is an enlarged fragmentary elevational view of a catheter tip of second embodiment shown in substantially closed position.

DETAILED DESCRIPTION OF THE PREFERRED EMBODIMENT

Figure 8:
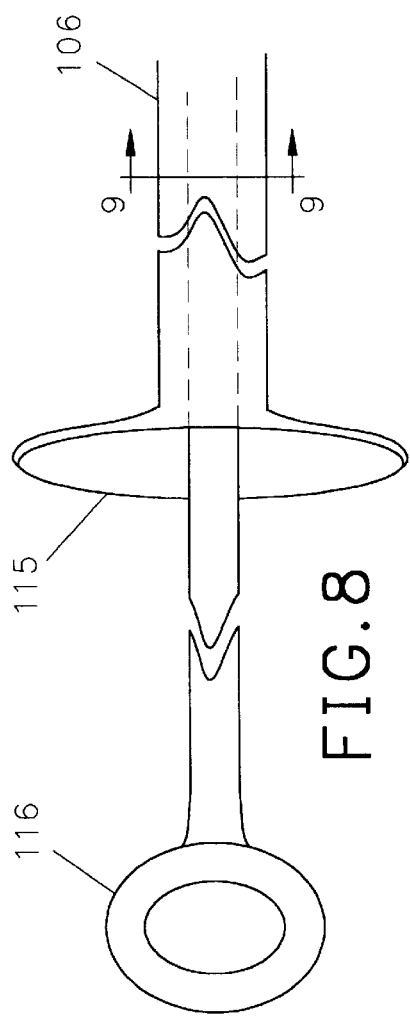
FIG. 8 is an enlarged fragmentary perspective view of the proximal end of the catheter tube.

Referring to FIG. 1, a catheter, generally indicated at 10, constructed in accordance with the present invention, includes a hollow tubular body 11 which is made of a flexible but dimensionally stable material and includes at a distal end thereof a catheter tip, generally indicated at 11a. Tip 11a includes a pair of hollow semi-frustoconically shaped tips 12, 13 made of rigid material such as metal, rigid plastic, or the like, which are connected to the body 11 by an elastic foraminous bridging portion 14.

Referring to FIG. 2, in the hollow center of the catheter body 11, a control rod 15 extends from a proximal end of the catheter (not shown) to the distal tip 11a. The rod 15 may have a scale which is larger relative to the diameter of the catheter body 11 than shown in the drawings. A small diameter rod 15 allows one to more clearly see the surrounding catheter structure. At the distal end of the control rod 15, a pair of arms 16, 17 are pivotally mounted to extend therefrom. At their opposing distal ends, arms 16, 17 are pivotally mounted to the hollow interior of the semi-frustoconical tips 12, 13, at pivot mountings 12a, 13a, respectively. As shown in FIGS. 1 and 2, the distal end of the catheter is depicted in partially open position. In a closed position, the side edges 18, 18a, 19, 19a, respectively, of the semi-frustoconical tips 12, 13, are contiguous touching one another. In order to provide a safe distal end to catheter tip 11, semi-lumen shape (shaped, elongated) leading edges 28, 29 are somewhat blunt to prevent the rupture of a vessel wall when probing with the catheter tip. The positioning of the distal end 15a of rod 15 is such that when the jaws of the semi-frustoconical tips 12, 13, respectively, are in closed position, the control arms 16, 17, respectively, will preferably have some vector component perpendicular to the axis of control rod 15 to provide a substantial perpendicular force when the rod 15 is displaced toward the distal end of the semi-frustoconical tips. The catheter tips may be sized to provide a tip maximum diameter of 1 mm, 2 mm, or the like, for use in stenotic structures of varying diameters.

While the catheter body 11 is made of a dimensionally stable but pliable material suitable for bending along the interior luminal walls, and the semi-frustoconical tips 12, 13, respectively, are made of a rigid material, the bridging portion 14 therebetween is made of an elastic material to allow the semi-frustoconical tips to extend outwardly during the expansion of the tip 11a and yet maintain outer surface continuity with the catheter body 11. Additionally, if desired, a thin foraminous elastic sheath (not shown) may be extended over the outside of body 11 and tip 11a. Elastic bridging portion 14 is attached to the distal end of the catheter body 11 at end wall 20, and is attached to the rear semicircular edges 21, 22 of the semi-frustoconical tips 12, 13, respectively. The flexible body of the elastic bridging portion 14 has apertures 23—23, and a pair of circular enlarged bight portion 24–25, one positioned on each side of the bridging portion, to aid in the bridging portion acting as an elastic hinge between the opposed semi-frustoconical tips 12, 13, respectively, when they are moved from a closed to an open position and vice versa.

Each of the rigid semi-frustoconical tips 12, 13 includes a semi-frustoconical outer surface 26, 27, respectively, a semicircular leading edge 28, 29, respectively, at the forward distal end of each of the tips. The aforementioned opposed side edges 18, 19 and 18a, 19a meet when the tips are together in closed position, and the trailing semicircular edges 21, 22 are joined to forward edges of the elastic bridging portion 14.

Referring to FIG. 3, the catheter 10 of the invention is shown in an open position with control rod 15 pushed forward relative to the distal end of the tip 11a such that the arms 16 and 17 are substantially perpendicular to the control rod, or in the preferred embodiment, at least in more of a perpendicular position to the control rod than in the almost closed position shown in FIG. 2. When in the open position, the semi-frustoconical tips 12, 13 are pushed radially outwardly 6f the control rod 15 such that the distal ends 28, 29, respectively, and their trailing semicircular edges 21, 22, respectively, are moved generally perpendicularly outwardly from the axis of the catheter 11. With the outward radial movement of the trailing semicircular edges 21, 22 of the semi-frustoconical tips 12, 13, respectively, the bight portions 24, 25, of the elastic bridging portion 14 are stretched to allow the provision of a continuous surface from the tips 12, 13, respectively, to the body 11 of the catheter 10. The bridging portion 14 acts to restrain movement of the tip trailing edges 21, 22 preventing undue excess pivotal movement of the tips around the distal ends of arms 16, 17.

In an important aspect of the present invention, the semicircular leading edges 28, 29 of each of the tips 12, 13 together with the apertures 23—23 in bridging portion 14 provide a passageway for blood or other body fluids to continue to flow through the structure even when the catheter tip is in the expanded position shown in FIG. 3. This is a substantial improvement over prior art balloon catheters which block or occlude the flow of fluid through the vessel while the balloon is in an expanded position. While the balloon catheter may only be expanded for short discrete periods of time in the blood vessel, the catheter 10 of the present invention may have its tip expanded for an indeterminate length of time as necessary to open the stenotic lumen portion of the blood vessel. Additionally, the opening catheter tip of the invention allows a surgeon to enlarge a stenotic vessel in piecemeal fashion. As a portion of a stenotic structure is opened, the tip may be further extended along the narrowed vessel and re-expanded multiple numbers of times to enlarge longer sections of the vessel.

FIG. 4 shows the control rod 15 as having a distal end with pivotally mounted arms 16, 17, pivotally mounted thereto, and a proximal end 30 which is enlarged to provide for finger pressure thereon to push the control rod 15 into the tubular body 11 of the catheter 10.

The catheters 10 and 100 of the invention have additional uses in other dilatation procedures opening stenotic lumens in other body organ systems, and blood vessels in places other than around the heart.

Referring to FIGS. 5, 6 and 7, a second embodiment of the preferred invention is generally indicated at 100. The second embodiment of the invention, similarly to the first embodiment shown at 10, includes a pair of semi-frustoconical lumens 101, 102. However, where the semi-frustoconical lumens 11, 12 of the first embodiment were held together by an elastic bight portion 14, semi-frustoconical lumens 101 and 102 are pivotally mounted together by hinges 103, 104, respectively. The resilient bight portion 14 in the first embodiment is replaced by a resilient sheath 105 in the second embodiment which extends over the semi-frustoconical lumens 101, 102, between the lumens and the catheter tube 106 and a portion of the catheter tube. The portion of the sheath 105 which is positioned between the semi-frustoconical tips 101 and 102 and the catheter tube 105 is constructed with a plurality of apertures 106—106 therethrough for allowing the passage of blood or other body fluids through the distal end of the dilatation tip while medical procedures are ongoing. The resilient nature of the sheath 105 allows the tips 101, 102 to expand from the position substantially closed in FIG. 7 to the open position in FIG. 6 repeatedly, i.e., the amount of expansion of the sheath at the tips is within the elastic range of the resilient properties of the sheath 105.

Referring to FIGS. 6, 7, 8 and 10, control rod 108 serves the same function as control rod 15 in the first embodiment. The distal end 109 of control rod 108 includes a mounting in which rigid arms 110, 111 are pivotally connected at one of their respective ends while their opposing ends 112, 113 are pivotally mounted on the interior of the semi-frustoconical lumens 101, 102, respectively. FIG. 7 shows the control rod 108 and the connecting arms 110, 111 in a mainly closed position, and FIG. 6 shows the control rod 108 and the connecting arms 110, 111 in an open position in the preferred orientation.

Figure 10:
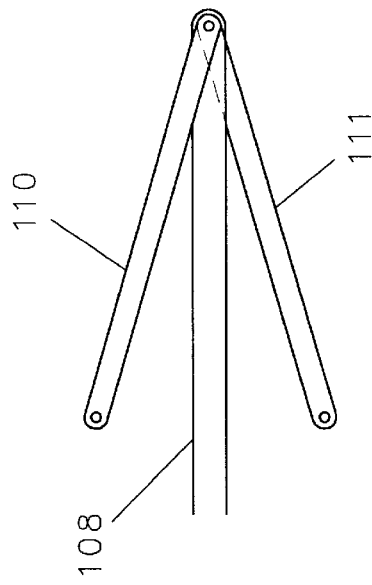
FIG. 10 is a detailed fragmentary view of the operator rod and linkage shown for use in a reversed (pulling) arrangement.

FIG. 10 shows a second orientation of the control rod 108 and connecting arms 110, 111 positioned in what would be a closed orientation of the semi-frustoconical lumens 101, 102, respectively. In this orientation, the control rod 108 is positioned forwardly when the lumens 101, 102 are in closed position and the rod 108 would be pulled at the proximal end of the catheter to open the lumens. In the orientation shown in FIG. 7, the control rod is pushed to open the lumens. Depending upon the desirability of the procedure, the push or pull orientation may be utilized to operate the opening of the lumens in accordance with the present invention. However, it should be noted that in the orientation shown in FIG. 10, there is less space for blood or other body fluids to flow through the open tip of the semi-frustoconical lumens.

Figure 9:
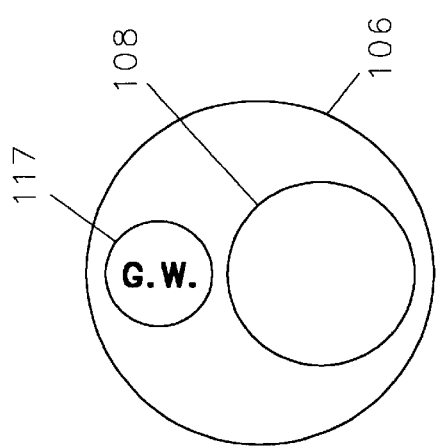
FIG. 9 is a cross-section view taken substantially along line 9—9 of FIG. 8 showing a guide wire also inserted through the catheter tube.

Referring to FIGS. 8 and 9, the catheter 106 is shown at its proximal end 115 which includes a radially extending flange suitable for grasping by the fingers of a user. The proximal end of control rod 108 includes a radial flange 116 which is used or controlled by thumb pressure in the case of the second embodiment shown in FIGS. 6 and 7 and is controlled by finger pulling in the case of the control rod operated as shown in FIG. 10.

FIG. 9 is a cross section of a modification of the second embodiment of the invention which utilizes a guide wire 117 positioned alongside the control rod 108 within the catheter 106. Guidewires such as 117 are commonly used in dilatation catheter techniques. In this instance, the guidewire passes from the proximal end 115 of catheter 106 through the catheter and out the hole formed by the leading edges of 101a, 102a of the semi-frustoconical lumens. The guidewire is passed through a vessel or structure area in which the catheter is to be positioned, and the catheter follows the guidewire along the vessel. In this embodiment, the guidewire is fed and controlled from the proximal end of the catheter. Use of the guidewire in this embodiment does not disrupt the flow of blood through the distal end of the catheter.

While two embodiments of the present invention have been shown and described, it will be apparent to those skilled in the art that many changes and modifications may be made without departing from the true spirit and scope of the present invention. It is the intent of the appended claims to cover all such changes and modifications which fall within the true spirit and scope of the invention.

What is claimed:

1. A dilatation catheter for use in angioplasty and other lumenal dilatation procedures, an expandable lumen distal tip comprising,
   a pair of substantially rigid semi-conical jaw means positioned adjacent a distal end of said catheter for providing a controllable mechanical expansion of the distal tip of said catheter,
   hinge means positioned between each of said pair of jaw means for restraining movement of a base of each of said jaw means relative to the other of said jaw means,
   control means for expanding and contracting a distal end of said jaw means from a position remote from said expandable lumen distal tip, and
   fluid passageway means therethrough for providing a path for fluid flow through said expandable lumen tip while said catheter is being used.

2. The dilatation catheter as defined in claim 1 wherein said control means includes,
   an elongate tubular body extending from said jaw means at a distal end thereof to an opposing proximal end,
   a control rod positioned through said tubular body and extending outwardly of said proximal end thereof, and
   means between a distal end of said control rod for changing axial motion of said control rod into radial motion of said pair of semi-conical jaw means.

3. The dilatation catheter as defined in claim 1 wherein said fluid passageway means include a hollow interior from front to back on each of said pair of said semi-conical jaw means and said hinge means include a foraminous resilient tubular member for allowing fluid to flow from outside said catheter, therethrough, and through said hollow interior of said semi-conical jaw means.

4. The dilatation catheter as defined in claim 2 further including,
   a guide wire extendable through said expandable lumen distal tip, and said tubular body.

5. The dilatation catheter as defined in claim 1 wherein said pair of semi-conical jaw means include,
   two hollow tips each including a semi-lumen leading edge, a semi-frustoconical shape body rearwardly of said leading edge, an interior surface of said semi-frustoconical shape body including a pivotal mounting, said body including a pair of opposing converging side edges, and a semi-lumen shape base defining the rear of said tip.

6. The dilatation catheter as defined in claim 5 further including a guidewire extending through said tubular body, said jaw means and out of said semi-lumen leading edges thereof, and also out said proximal end of said tubular body.

7. A dilatation catheter for use in angioplasty and other lumenal dilatation procedures including an expandable lumen distal tip comprising,
   a pair of semi-conical jaw means positioned adjacent a distal end of said catheter for providing a controllable mechanical expansion of the distal tip of said catheter,
   said pair of semi-conical jaw means include,
   two hollow tips each including a semi-lumen leading edge, a semi-frustoconical shape body rearwardly of said leading edge, an interior surface of said hollow tip body including a pivotal mounting, said body including a pair of opposing converging side edges, and a semi-lumen shape base defining the rear of said tip,
   hinge means positioned between each of said pair of jaw means for restraining movement of said of each of said jaw means relative to the other of said jaw means,
   said hinge means including
   a resilient tubular member extending from said distal end of said elongate tubular body to said rear semi-lumen shape base edges of said pair of hollow tips, and a pair of bight portions positioned between each of said tip base edges,
   control means for expanding and contracting a distal end of said jaw means from a position remote from said expandable lumen distal tip,
   said control means include,
   an elongate tubular body extending from said jaw means at a distal end thereof to an opposing proximal end,
   a control rod positioned through said tubular body and extending outwardly of said proximal end thereof, and means between a distal end of said control rod for changing axial motion of said control rod into radial motion of said pair of semi-conical jaw means.

8. The dilatation catheter as defined in claim 7 wherein said hinge means includes, a pair of pivotal hinges, each positioned at a juncture of said semi-lumen base edge and one of said converging side edges of said semi-frustoconical shape body, and forming a bight portion between said pair of hollow tips.

9. The dilatation catheter as defined in claim 7 wherein said resilient tubular member is foraminous for allowing fluid to pass therethrough and through said hollow tips.

10. The dilatation catheter as defined in claim 7 further including, means for providing fluid flow through at least said distal end of said catheter during dilatation procedures.

11. A dilatation catheter for use in angioplasty and other lumenal dilatation procedures including an expandable lumen distal tip comprising, a pair of semi-conical jaw means positioned adjacent a distal end of said catheter for providing a controllable mechanical expansion of the distal tip of said catheter, wherein said pair of semi-conical jaw means include, two hollow tips each including a semi-lumen leading edge, a semi-frustoconical shape body rearwardly of said leading edge, an interior surface of said hollow tip body including a pivotal mounting, said body including a pair of opposing converging side edges, and a semi-lumen shape base defining the rear of said tip, hinge means positioned between each of said pair of jaw means for restraining movement of said base of each of said jaw means relative to the other of said jaw means, control means for expanding and contracting a distal end of said jaw means from a position remote from said expandable lumen distal tip, said control means including an elongate tubular body extending from said jaw means at a distal end thereon to an oposing proximal end, and a resilient sheath positioned over said jaw means, between said jaw means and said elongate tubular body and over at least a portion of said elongate tubular body.

12. The dilatation catheter as defined in claim 11 wherein said sheath is foraminous.

13. A dilatation catheter for use in angioplasty and other lumenal dilatation procedures including an expandable lumen distal tip comprising, a pair of semi-conical jaw means positioned adjacent a distal end of said catheter for providing a controllable mechanical expansion of the distal tip of said catheter, wherein said pair of semi-conical jaw means include, two hollow tips each including a semi-lumen leading edge, a semi-frustoconical shape body rearwardly of said leading edge, an interior surface of said hollow tip body including a pivotal mounting, said body including a pair of opposing converging side edges, and a semi-lumen shape base defining the rear of said tip, hinge means positioned between each of said pair or jaw means for restraining movement of said base of each of said jaw means relative to the other of said jaw means, control means for expanding and contracting a distal end of said jaw means from a position remote from said expandable lumen distal tip, said control means including an elongate tubular body extending from said jaw means at a distal end thereon to an opposing proximal end, a resilient sheath positioned over said jaw means, between said jaw means and said elongate tubular body and over at least a portion of said elongate tubular body, and fluid passageway means therethrough for providing a path for fluid flow through said expandable lumen distal tip while said catheter is being used.

14. A dilatation catheter for use in angioplasty and other lumenal dilatation procedures including an expandable lumen distal tip comprising, a pair of semi-conical jaw means positioned adjacent a distal end of said catheter for providing a controllable mechanical expansion of the distal tip of said catheter, said pair of semi-conical jaw means include, two hollow tips each including a semi-lumen leading edge, a semi-frustoconical shape body rearwardly of said leading edge, an interior surface of said hollow tip body including a pivotal mounting, said body including a pair of opposing converging side edges, and a semi-lumen shape base defining the rear of said tip, hinge means positioned between each of said pair of jaw means for restraining movement of said base of each of said jaw means relative to the other of said jaw means, said hinge means including a resilient tubular member extending from said distal end of said elongate tubular body to said rear semi-lumen shape base edges of said pair of hollow tips, and a pair of bight portions positioned between each of said tip base edges, control means for expanding and contracting a distal end of said jaw means from a position remote from said expandable distal lumen tip, said control means include, an elongate tubular body extending from said jaw means at a distal end thereof to an opposing proximal end, a control rod positioned through said tubular body and extending outwardly of said proximal end thereof, means between a distal end of said control rod for changing axial motion of said control rod into radial motion of said pair of semi-conical jaw means, and fluid passageway means therethrough for providing a path for fluid flow through said expandable lumen distal tip while said catheter is being used.

* * * * *